(12) United States Patent
Ofori et al.

(10) Patent No.: US 7,002,046 B2
(45) Date of Patent: Feb. 21, 2006

(54) PROCESS FOR THE RECOVERY OF DIHYDROXYBIARYL COMPOUNDS

(75) Inventors: John Yaw Ofori, Niskayuna, NY (US); Ben Purushotam Patel, Niskayuna, NY (US); Eric James Pressman, East Greenbush, NY (US)

(73) Assignee: General Electric Company, Schenectady, NY (US)

( * ) Notice: Subject to any disclaimer, the term of this patent is extended or adjusted under 35 U.S.C. 154(b) by 251 days.

(21) Appl. No.: 10/680,776

(22) Filed: Oct. 7, 2003

(65) Prior Publication Data

US 2005/0075519 A1    Apr. 7, 2005

(51) Int. Cl.
*C07C 39/12* (2006.01)

(52) U.S. Cl. .................................... 568/730

(58) Field of Classification Search ................ 568/730
See application file for complete search history.

(56) References Cited

U.S. PATENT DOCUMENTS 5,177,258 A     1/1993  Becker et al. ............... 562/488
6,833,482 B1 *  12/2004 Patel et al. .................. 568/730

OTHER PUBLICATIONS

Abstarct of JP 01-224,330 (1989).*
Abstarct of JP 01-299,236 (1989).*
Abstarct of JP 02-053,749 (1989).*
Abstarct of JP 62-026,238 (1987).*
Abstarct of JP 61-137,838 (1986).*
M. Bush et al, "Formation of Carbon Chains in the Catalytic Reduction of Alkyl Halogen Compounds"; *J. Prakt. Chem.* 146, 1-55 (1936) (and English abstract), No Translation.
M Busch and W. Schmidt, "Catalytic Hydrogenation of Organic Halogen Compounds"; *Chemische Berichte.* 62, 2612-2620 (1929) (and English abstract), No Translation.

* cited by examiner

*Primary Examiner*—Michael L. Shippen
(74) *Attorney, Agent, or Firm*—Martha L. Boden, Esq.; Heslin Rothenberg Farley & Mesiti, P.C.

(57) ABSTRACT

A method for preparing and isolating dihydroxybiaryl compounds, such as 4,4'-dihydroxybiphenyl, is disclosed. The alkali metal salt of the dihydroxybiaryl compound is protonated with the monohydroxyaryl halide compound initially used in the reductive coupling reaction which produced the alkali metal salt. In addition, the alkali metal salt of the monohydroxyaryl halide compound is produced by the process, which can then be recycled as the base and monohydroxyaryl halide in a further reductive coupling reaction to form the alkali metal salt of the dihydroxybiaryl compound.

24 Claims, No Drawings

PROCESS FOR THE RECOVERY OF DIHYDROXYBIARYL COMPOUNDS

CROSS-REFERENCE TO RELATED APPLICATIONS

This Application is related to the following U.S. patent application: U.S. patent application Ser. No. 10/681,492 now U.S. Pat. No. 6,833,482 entitled "METHOD FOR PRODUCTION OF BIS(HYDROXY-AROMATIC) COMPOUNDS" which is hereby incorporated herein by reference in its entirety.

BACKGROUND OF THE INVENTION

This invention relates to the reductive coupling of monohydroxyaryl halide compounds, and more particularly, to the isolation and recovery of dihydroxybiaryl compounds formed from such reactions.

Dihydroxybiaryl compounds, including dihydroxybiphenyls, such as 4,4'-dihydroxybiphenyl (also referred to herein as "biphenol") and 2,2'-dimethyl-4,4'-dihydroxybiphenyl (also referred to herein as "dimethyl biphenol") have numerous uses in the chemical industry. For example, biphenol can be used in polymer preparation, notably in the preparation of polycarbonates, polysulfones, polyimides, and polyetherimides.

Dihydroxyaryl compounds can be prepared by the reductive coupling of monohydroxyaryl halides, as described in U.S. Pat. No. 5,177,258. Briefly, in the synthesis of biphenol, for example, p-bromophenol is contacted with a reducing agent, such as formic hydrazide or hydrogen, in the presence of an aqueous base, such as sodium hydroxide, and a platinum group catalyst, preferably palladium, which may be supported on carbon. The p-bromophenol is supplied to the reaction with enough base to form the Na-salt, prior to coupling, and after the reaction is complete, to have the biphenol formed exist as the Na-salt. Isolation of biphenol requires protonation of the Na-salt with an acid, such as hydrochloric acid. This is problematic, in part, because introduction of excess acid to the system requires additional processing for its removal after biphenol is formed. Furthermore, when HCl is used for protonation, for example, the Na salt of the acid (NaCl) is formed as a by-product. When produced on a commercial scale, NaCl is expensive to handle and to dispose of.

Thus, improved methods for the isolation of dihydroxybiaryl compounds from their alkali metal salts continue to be sought. In particular, it would be advantageous to avoid the introduction of a foreign acid, such as HCl, to protonate the salt of the dihydroxybiaryl compound. Such a process would be more economical because fewer reagents would need to be purchased and because excess acid would not need to be removed from the system. Furthermore, isolation of the desired dihydroxybiaryl compound would be simplified because the need for additional processing operations to handle the mixture resulting from the use of the foreign acid could be eliminated. It would also be cost-effective in large scale commercial operations if the base represented by the Na salt of the dihydroxybiaryl compound in the product mixture could be recycled in a further reductive coupling reaction of the monohydroxyaryl halide to form the dihydroxybiaryl compound, instead of being neutralized to form water, as is the case when HCl is used.

SUMMARY OF THE INVENTION

The present invention provides a novel and efficient method for preparing dihydroxybiphenyls from their alkali metal salts. Unlike previous techniques, the present method unexpectedly avoids the use of a foreign acid to protonate the salt of the dihydroxybiphenyl, such as the sodium salt of biphenol, by employing the monohydroxyaryl halide used in the initial reductive coupling reaction. In addition, the process yields a base, i.e., the alkali metal salt of the monohydroxyaryl halide, which can be recycled in a further reaction to make the dihydroxybiphenyl.

Therefore, in one aspect, the present invention relates to a method for preparing a dihydroxybiaryl compound. The method comprises providing an alkali metal salt of the dihydroxybiaryl compound, followed by contacting the alkali metal salt of dihydroxybiaryl compound with a corresponding monohydroxyaryl halide compound.

In another aspect, the method of the present invention relates to isolating a dihydroxybiaryl compound comprising providing an alkali metal salt of the dihydroxybiaryl compound, followed by contacting the salt with a corresponding monohydroxyaryl halide compound to form a precipitate in a solution. The precipitate, which comprises the dihydroxybiaryl compound, is then separated from the solution.

DETAILED DESCRIPTION OF THE INVENTION

Dihydroxybiaryl compounds, which can be prepared by the present method, may be substituted or unsubstituted. Particularly useful dihydroxybiaryl compounds include 4,4'-dihydroxybiphenyl ("biphenol") and 2,2'-dimethyl-4,4' dilhydroxybiphenyl ("dimethyl biphenol"). However, the invention is not limited to the preparation of these compounds, and other dihydroxybiaryl derivatives may be prepared by the present method, as would be obvious to one of skill.

Initially, according to the present method, the alkali metal salt of the desired dihydroxybiaryl compound is provided. There are many known methods for the production of the alkali metal salt. Conventional synthetic methods include the reductive coupling of hydroxyaryl halide compounds using a base, such as KOH or NaOH, a metallic catalyst, such as Pd, Rh, Ru, or Ni, and a reducing agent, such as hydrogen, sodium formate, paraformaldehyde, glycols, glycerol, methanol, or formic hydrazide, for example. Typically, the reaction is run at a temperature ranging from about 20° C. to about 120° C. A molar ratio of the base to the monohydroxyaryl halide of at least 1:1 is employed, and the amount of the catalyst needed ranges from about 0.01 and 5% of the weight of the monohydroxyaryl halide. When formic hydrazide is employed as the reductant, a molar ratio of formic hydrazide to the monohydroxyaryl halide ranging from about 1:4 to about 1:1 is suitable. Such processes are described fully in the aforementioned U.S. Pat. No. 5,177,258. Scheme 1 depicts a conventional process for preparing the sodium salt of biphenol (I) by the reductive coupling of p-bromophenol (II).

Scheme 1

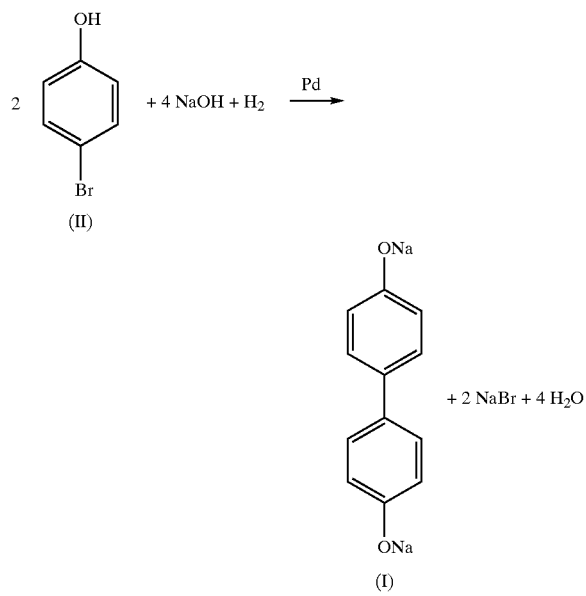

The alkali metal salt of the dihydroxybiaryl compound is then contacted with a corresponding monohydroxyaryl halide compound, i.e. one which could be used in the aforementioned reductive coupling reaction to form the alkali metal salt of the dihydroxybiaryl compound. The corresponding monohydroxyaryl halide compound protonates the alkali metal salt of the dihydroxybiaryl compound, thereby producing the desired dihydroxybiaryl product. Typically the protonation reaction occurs at a temperature ranging from about 20° C. to about 120° C. A molar ratio of the monohydroxyaryl halide to the alkali metal salt of the dihydroxybiaryl compound of at least 2:1 maximizes the amount of dihydroxybiaryl product.

When the reaction is complete, a precipitate containing the desired dihydroxybiaryl compound is produced. Generally, the reaction is performed below the melting point of the dihydroxybiaryl compound and the dihydroxybiaryl compound is substantially insoluble in the reaction solution matrix. For example, the melting point of biphenol is 282–284° C. The precipitate can then be separated and removed from the remaining solution, typically by filtration, to isolate the product. If desired, the solid precipitate can be washed with water or methanol one or more times. The precipitate can then be transformed into a purified dihydroxybiaryl compound by recrystallizing the precipitate in methanol, for example. As used herein, the term "purified" means having a purity of at least 90 percent, preferably greater than 95 percent, and still more preferably greater than 98 percent.

In one embodiment, biphenol may be prepared by providing one molar equivalent of the sodium or potassium salt of 4,4'-dihydroxybiphenyl having formula (I), and contacting (I) with at least two molar equivalents of p-bromophenol having structure (II) to form one equivalent of 4,4'-dihydroxybiphenyl (III), which precipitates from solution, and two molar equivalents of the sodium salt of p-bromophenol (IV) according to the following Scheme 2:

Scheme 2

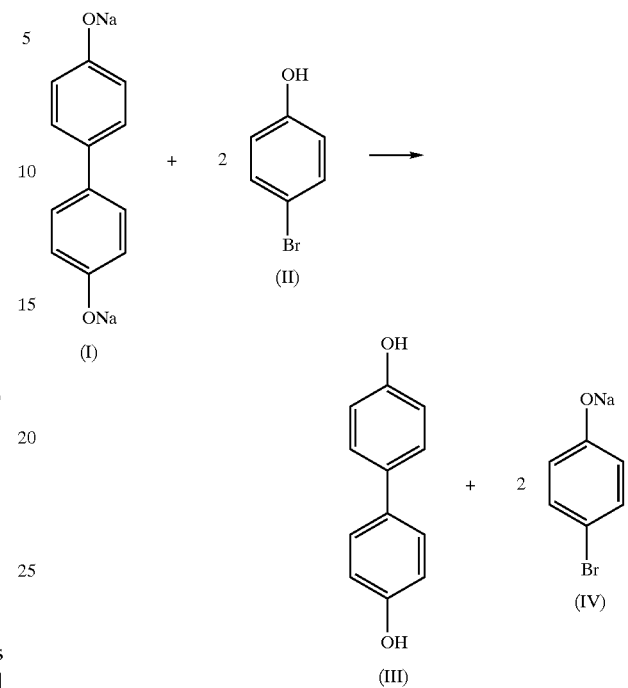

Alternatively, in the production of biphenol, p-chlorophenol could be substituted for p-bromophenol (II) in the reaction depicted in Scheme 2. In this case, protonation using the chloro-compound, which is slightly more acidic than the corresponding bromo-compound, is at least as effective in acidification compared to the bromophenol.

Other embodiments include protonation of the alkali metal salt of dimethyl biphenol using 2-methyl-4-bromophenol or 2-methyl-4-chlorophenol. 2-Methyl-4-bromophenol and 2-methyl-4-chlorophenol are monohydroxyaryl halides suitable for use in the aforementioned reductive coupling reaction to form dimethyl biphenol.

The filtrate, containing the alkali metal salt of the monohydroxyaryl halide, can then be recycled as one equivalent of the monohydroxyaryl halide and one equivalent of the base in a further reductive coupling of the monohydroxyaryl halide to form additional dihydroxybiaryl compound, similar to the reaction described in the previously discussed U.S. Pat. No. 5,177,258 and depicted in Scheme 1. The filtrate solution, along with an alkali metal hydroxide, such as sodium hydroxide or potassium hydroxide, is contacted with a metal catalyst, such as palladium, and a reducing agent, such as hydrogen gas, which may be bubbled into the reaction mixture or introduced under pressure up to about 100 atm, or formic hydrazide, in water to produce the alkali metal salt of the desired dihydroxybiaryl compound. Additional amounts of the monohydroxyaryl halide compound may optionally be added, but generally, the monohydroxyaryl halide initially added in the precipitation is used in the subsequent reaction to make the dihydroxybiaryl compound. Scheme 3 depicts the present process of the invention for recycling the sodium salt of p-bromophenol (IV) produced in the protonation process depicted in Scheme 2 in the reductive coupling of p-bromophenol to form additional amounts of the sodium salt of biphenol.

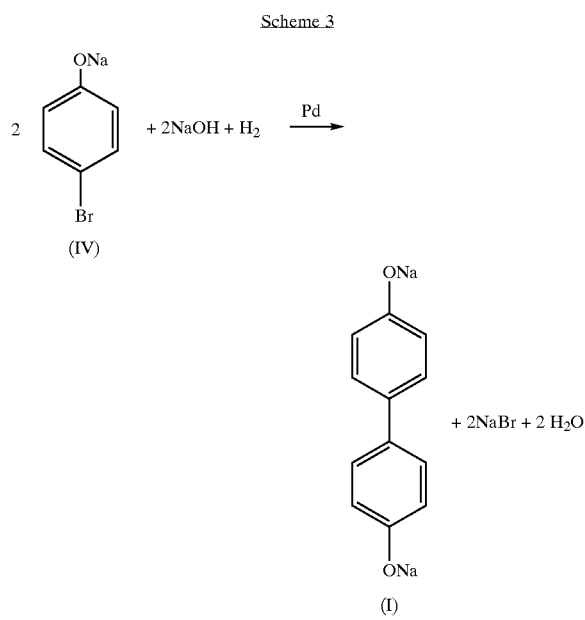

Scheme 3

Briefly, the metal catalyst, preferably 5% palladium on carbon is initially stirred into a solution containing NaOH or KOH and the filtrate containing the alkali metal salt of the hydroxyaryl halide compound. The amount of palladium catalyst used is between about 0.01 and 5% of the weight of the alkali metal salt of the monohydroxyaryl halide. To this solution, the reducing agent is added. When formic hydrazide is used, a molar ratio of formic hydrazide to the alkali metal salt of the hydroxyaryl halide ranging from about 1:4 to about 1:1 is typical. When hydrogen gas is used as the reductant, it is generally flowed through the solution at a pressure ranging from about 1 atm to about 100 atm. In one embodiment, hydrogen gas is employed at a pressure ranging from about 1 atm to about 350 kilopascals, as described in the related U.S. patent application Ser. No. 10/681,492 entitled "METHOD FOR PRODUCTION OF BIS(HYDROXY-AROMATIC) COMPOUNDS" The reaction is typically run at a temperature ranging from about 20°–120° C., and the alkali metal salt of the dihydroxybiaryl compound is produced again. In the present process, a molar ratio of the alkali metal hydroxide to the alkali metal salt of the monohydroxyaryl halide of at least 1:1 maximizes the production of the alkali metal salt of the dihydroxybiaryl compound. The procedure outlined above for protonating the alkali metal salt of the dihydroxybiaryl compound with the monohydroxyaryl halide compound can then be followed again.

In the above Scheme 2, the sodium salt of p-bromophenol (IV) (or the alkali metal salt of p-chlorophenol, not shown) is formed in the filtrate, which can then be used as one equivalent of the base and one equivalent of the monohydroxyaryl halide, in the preparation of biphenol (sodium salt initially) by the reductive coupling of p-bromophenol (or p-chlorophenol), shown in Scheme 3. In other embodiments, the sodium or potassium salt of 2-methyl-4-bromophenol or 2-methyl-4-chlorophenol may be formed in the filtrate, each of which could then be used as the base in a coupling reaction with 2-methyl-4-bromophenol or 2-methyl-4-chlorophenol, respectively, to form dimethyl biphenol.

The following examples are given by way of illustration and are not intended to be limitative of the present invention. The reagents, reactants, and catalysts used in the reactions described herein are readily available materials.

EXAMPLE 1

To a round bottom flask equipped with a magnetic stir bar was charged 1.073 g (5.76 mmol) of biphenol and 0.476 g (11.9 mmol) of NaOH and 9.102 g of water. A clear yellowish solution containing the sodium salt of biphenol was formed.

EXAMPLE 2

To the solution containing the sodium salt of biphenol from Example 1, 2.09 g (12.08 mmol) of p-bromophenol were added, and a precipitate formed. The solution containing the precipitate was then filtered, and the solid was recovered. HPLC analysis of the solid indicated that it contained 94.2% biphenol. Approximately, 0.8603 g were recovered, representing a 76% overall recovery.

EXAMPLE 3

The procedure of Example 2 was followed, except that prior to filtering, 9.91 g of water and 1.29 g of methanol were added to the solution to assist in preventing phase separation, and a fraction of the resulting solution (5.68 g) was filtered to separate the solid. An excess of 37% HCl (0.5695 g, molar amount needed to neutralize base was 0.2824 g) was added to the filtrate to neutralize all the base present, and the pH was measured to be around 0. The resulting solution had a small amount of solid present, and 8.245 g of methanol were added to achieve complete dissolution. This solution was then analyzed by HPLC for biphenol and p-bromophenol. The analysis showed the ratio of p-bromophenol to biphenol to be around 20:1 (3.41% to 0.17%) by weight, compared with the expected number of about 2:1 (2.09:1.073=1.94:1) if protonation had not occurred. The expected p-bromophenol concentration was 3.42%. The expected composition of biphenol if it were all still present would be 1.75%. This indicates that the majority of the biphenol present was eliminated by the precipitation process (90% precipitation of biphenol).

EXAMPLE 4

A coupling reaction to produce biphenol is performed by charging a round bottom flask equipped with a magnetic stir bar with 0.6 part of palladium catalyst (5% by weight on carbon), 2.5 parts of the sodium salt of 4-bromophenol produced in the filtrate of Example 2, and 2.5 parts NaOH. After stirring for five minutes, 3 parts of formic hydrazide is added, and the mixture is stirred for 10 minutes. While stirring, the mixture is heated to 85° C., and the temperature is maintained for 30 minutes. Two and ½ parts (2.5) parts 4-bromophenol is then added, and a precipitate containing biphenol forms. The precipitate is filtered from the solution and washed with methanol. Purified biphenol having a purity of at least 90% is then obtained by recrystallizing the precipitate in methanol.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a dihydroxybiaryl compound comprising:
   (a) providing an alkali metal salt of said dihydroxybiaryl compound; and
   (b) contacting said alkali metal salt of said dihydroxybiaryl compound with a corresponding monohydroxyaryl halide compound.

2. The method of claim 1, wherein said dihydroxybiaryl compound is 4,4'-dihydroxybiphenyl.

3. The method of claim 2, wherein said corresponding monohydroxyaryl halide compound is p-bromophenol or p-chlorophenol.

4. The method of claim 2, wherein said alkali metal salt of said dihydroxybiaryl compound is the sodium salt of 4,4'-dihydroxybiphenyl or the potassium salt of 4,4'-dihydroxybiphenyl.

5. The method of claim 1, wherein said dihydroxybiaryl compound is 2,2'-dimethyl-4,4'-dihydroxybiphenyl.

6. The method of claim 5, wherein said corresponding monohydroxyaryl halide compound is 2-methyl-4-bromophenol or 2-methyl-4-chlorophenol.

7. The method of claim 5, wherein said alkali metal salt of said dihydroxybiaryl compound is the sodium salt of 2,2'-dimethyl-4,4'-dihydroxybiphenyl or the potassium salt of 2,2'-dimethyl-4,4'-dihydroxybiphenyl.

8. The method of claim 1, wherein a temperature ranging from about 20° C. to about 120° C. is employed.

9. The method of claim 1, wherein a molar ratio of said corresponding monohydroxyaryl halide compound to said alkali metal salt of said dihydroxybiaryl compound of at least 2:1 is employed.

10. The method of claim 1, further comprising after step (b), the steps of:
    (c) removing a precipitate formed by said contacting step from a solution formed by said contacting step, wherein said precipitate comprises said dihydroxybiaryl compound; and
    (d) recycling the remaining solution comprising an alkali metal salt of said monohydroxyaryl halide compound to form additional said alkali metal salt of said dihydroxybiaryl compound by contacting said remaining solution with a metal catalyst, an alkali metal hydroxide, and a reducing agent.

11. The method of claim 10, wherein said metal catalyst is palladium, and said reducing agent is formic hydrazide.

12. The method of claim 10, wherein said metal catalyst is palladium, and said reducing agent is hydrogen gas.

13. The method of claim 12, wherein said hydrogen gas is employed at a pressure ranging from about 1 atm to about 350 kilopascals.

14. The method of claim 10, wherein said alkali metal hydroxide is potassium hydroxide or sodium hydroxide.

15. The method of claim 10, wherein a temperature ranging from about 20° C. to about 120° C. is employed.

16. The method of claim 10, wherein said dihydroxybiaryl compound is 4,4'-dihydroxybiphenyl, said corresponding monohydroxyaryl halide compound is p-bromophenol or p-chlorophenol, and said alkali metal salt of said dihydroxybiaryl compound is the sodium salt of 4,4'-dihydroxybiphenyl or the potassium salt of 4,4'-dihydroxybiphenyl.

17. The method of claim 10, wherein said dihydroxybiaryl compound is 2,2'-dimethyl-4,4'-dihydroxybiphenyl, said corresponding monohydroxyaryl halide compound is 2-methyl-4-bromophenol or 2-methyl-4-chlorophenol, and said alkali metal salt of said dihydroxybiaryl compound is the sodium salt of 2,2'-dimethyl-4-4'-dihydroxybiphenyl or the potassium salt of 2,2'-dimethyl-4,4'-dihydroxybiphenyl.

18. The method of claim 10, wherein a molar ratio of said alkali metal hydroxide to said alkali metal salt of said monohydroxyaryl halide compound of at least 1:1 is employed.

19. A method for isolating a dihydroxybiaryl compound comprising:
    (a) providing an alkali metal salt of said dihydroxybiaryl compound;
    (b) contacting said alkali metal salt of said dihydroxybiaryl compound with a corresponding monohydroxyaryl halide compound to form a precipitate in a solution; and
    (c) separating said precipitate from said solution, wherein said precipitate comprises said dihydroxybiaryl compound.

20. The method of claim 19, wherein said dihydroxybiaryl compound is 4,4'-dihydroxybiphenyl, wherein said corresponding monohydroxyaryl halide compound is p-bromophenol or p-chlorophenol, and wherein said alkali metal salt of said dihydroxybiaryl compound is the sodium salt of 4,4'-dihydroxybiphenyl or the potassium salt of 4,4'-dihydroxybiphenyl.

21. The method of claim 19, wherein said dihydroxybiaryl compound is 2,2'-dimethyl-4,4'-dihydroxybiphenyl, wherein said corresponding monohydroxyaryl halide compound is 2-methyl-4-bromophenol or 2-methyl-4-chlorophenol, and wherein said alkali metal salt of said dihydroxybiaryl compound is the sodium salt of 2,2'-dimethyl-4,4'-dihydroxybiphenyl or the potassium salt of 2,2'-dimethyl-4,4'-dihydroxybiphenyl.

22. The method of claim 19, wherein a molar ratio of said corresponding monohydroxyaryl halide compound to said alkali metal salt of said dihydroxybiaryl compound of at least 2:1 is employed.

23. The method of claim 19, further comprising the step of washing said separated precipitate with water or methanol at least one time.

24. The method of claim 23, further comprising the step of recrystallizing said washed precipitate to provide a purified dihydroxybiaryl compound having a purity of at least 90%.

* * * * *